(12) United States Patent
Slipszenko et al.

(10) Patent No.: US 9,474,542 B2
(45) Date of Patent: Oct. 25, 2016

(54) ULTRASONIC TRANSDUCER SYSTEM

(71) Applicant: SRA DEVELOPMENTS LIMITED, South Devon (GB)

(72) Inventors: James Anton Slipszenko, South Devon (GB); Michael James Ede, South Devon (GB); Stephen Michael Radley Young, South Devon (GB)

(73) Assignee: SRA DEVELOPMENTS LTD., Ashburton, Devon (GB)

( * ) Notice: Subject to any disclaimer, the term of this patent is extended or adjusted under 35 U.S.C. 154(b) by 190 days.

(21) Appl. No.: 13/902,379

(22) Filed: May 24, 2013

(65) Prior Publication Data

US 2013/0253559 A1 Sep. 26, 2013

Related U.S. Application Data

(62) Division of application No. 12/994,037, filed as application No. PCT/GB2009/001281 on May 21, 2009, now abandoned.

(30) Foreign Application Priority Data

May 21, 2008 (GB) .................... 0809243.9

(51) Int. Cl.
*A61B 17/32* (2006.01)
*A61B 17/22* (2006.01)

(52) U.S. Cl.
CPC ............... *A61B 17/320068* (2013.01); *A61B 17/320092* (2013.01); *A61B 2017/22011* (2013.01);
(Continued)

(58) Field of Classification Search
CPC ............... A61B 17/22004; A61B 17/22012; A61B 17/2202; A61B 17/22029; A61B 17/320068; A61B 17/320092
See application file for complete search history.

(56) References Cited

U.S. PATENT DOCUMENTS 3,830,240 A * 8/1974 Antonevich et al. ......... 606/128
4,832,683 A   5/1989 Idemoto et al.
(Continued)

FOREIGN PATENT DOCUMENTS

EP  0970660 A1  1/2000
EP  1138264 A1  10/2001
(Continued)

OTHER PUBLICATIONS

PCT International Search Report dated Jan. 3, 2008 for PCT/GB2007/003560 filed Sep. 18, 2007.
(Continued)

*Primary Examiner* — Thomas McEvoy
(74) *Attorney, Agent, or Firm* — Heslin Rothenberg Farley & Mesiti P.C.

(57) ABSTRACT

A transducer stack (10) includes rings (16) of piezo-electric ceramic alternating with metal electrodes (18) along a threaded central shaft (32) extending from a titanium back plate (20). A spacer or threaded element (14) threaded on to the shaft (32) holds the ceramic rings (16) and electrodes (18) in compression against the back plate (20). The transducer stack (10) is mountable eccentrically to a horn (12) of an ultrasonically-vibratable tool, away from an axis of an elongate waveguide (56) extending from the horn (12). The transducer stack (10) may vibrate in a flexural mode perpendicular to the waveguide (56), generating torsional mode ultrasonic vibrations in the horn (12) and waveguide (56), or in a flexural mode parallel to the waveguide (56), generating longitudinal mode ultrasonic vibrations in the horn (12) and waveguide (56). The transducer stack (10) may be tuned by adjusting the length, mass and/or position along the shaft (32) of the threaded element (14), the back plate (20) and/or a second threaded element (410) mounted to the back plate (20). Motion sensors (22, 24) may be mounted to the horn (12). Torsional vibrational modes of the horn (12) and waveguide (56) may be identified by motion amplitude of a peripheral sensor (24) exceeding that of a near-axial sensor (22). The operation of the transducer stack (10) may be controlled in response thereto.

20 Claims, 12 Drawing Sheets

(52) U.S. Cl.
CPC ........... *A61B2017/22018* (2013.01); *A61B 2017/22024* (2013.01); *A61B 2017/22027* (2013.01); *A61B 2017/320072* (2013.01); *A61B 2017/320076* (2013.01); *A61B 2017/320096* (2013.01); *Y10T 29/49005* (2015.01)

(56) References Cited

U.S. PATENT DOCUMENTS

| | | | |
|---|---|---|---|
| 5,180,363 | A | 1/1993 | Idemoto et al. |
| 6,077,285 | A | 6/2000 | Boukhny |
| 6,283,981 | B1 | 9/2001 | Beaupre |
| 6,425,906 | B1* | 7/2002 | Young et al. ............ 606/169 |
| 2001/0001123 | A1 | 5/2001 | Madan et al. |
| 2002/0165577 | A1* | 11/2002 | Witt et al. ............ 606/205 |
| 2003/0045887 | A1 | 3/2003 | Sakurai et al. |
| 2005/0021065 | A1 | 1/2005 | Yamada et al. |
| 2007/0066978 | A1* | 3/2007 | Schafer et al. ............ 606/128 |
| 2009/0149801 | A1* | 6/2009 | Crandall et al. ............ 604/22 |

FOREIGN PATENT DOCUMENTS

| | | |
|---|---|---|
| EP | 1693027 A1 | 8/2006 |
| GB | 2333709 A | 8/1999 |
| GB | 2425480 A | 11/2006 |
| JP | 2003116863 A | 4/2003 |
| SU | 1388002 A1 | 4/1984 |
| WO | 01/21079 A1 | 3/2001 |
| WO | 01/52782 A1 | 7/2001 |
| WO | 03/082132 A1 | 10/2003 |

OTHER PUBLICATIONS

GB Search Report dated Nov. 29, 2007 for GB 0718476.5.
PCT International Preliminary Report on Patentability dated Mar. 24, 2009 for PCT/GB2007/003560 filed Sep. 18, 2007.
PCT International Preliminary Report on Patentability dated Sep. 11, 2007 for PCT/GB2006/000697.
International Search Report dated May 3, 2006 for PCT/GB2006/000697.
GB Search Report dated Jun. 27, 2006 for GB 0504321.1.

* cited by examiner

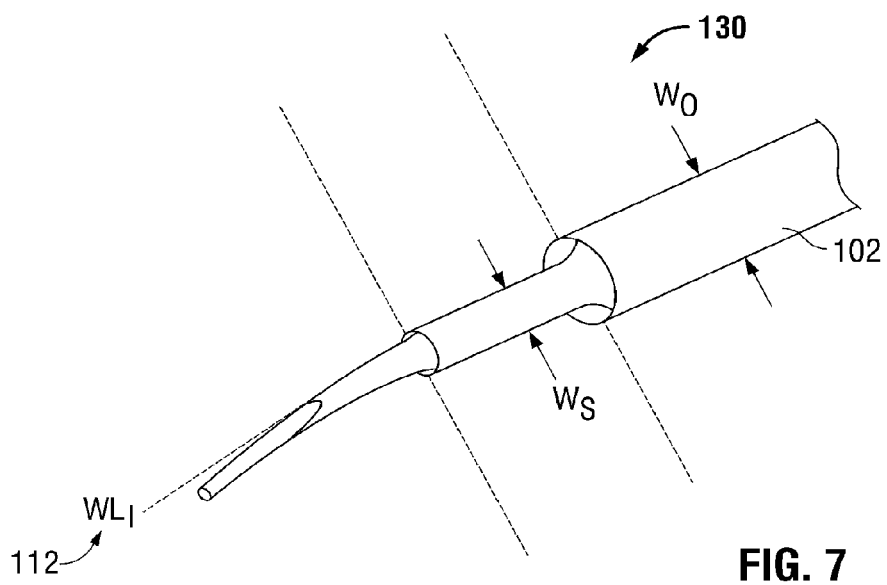
FIG. 7
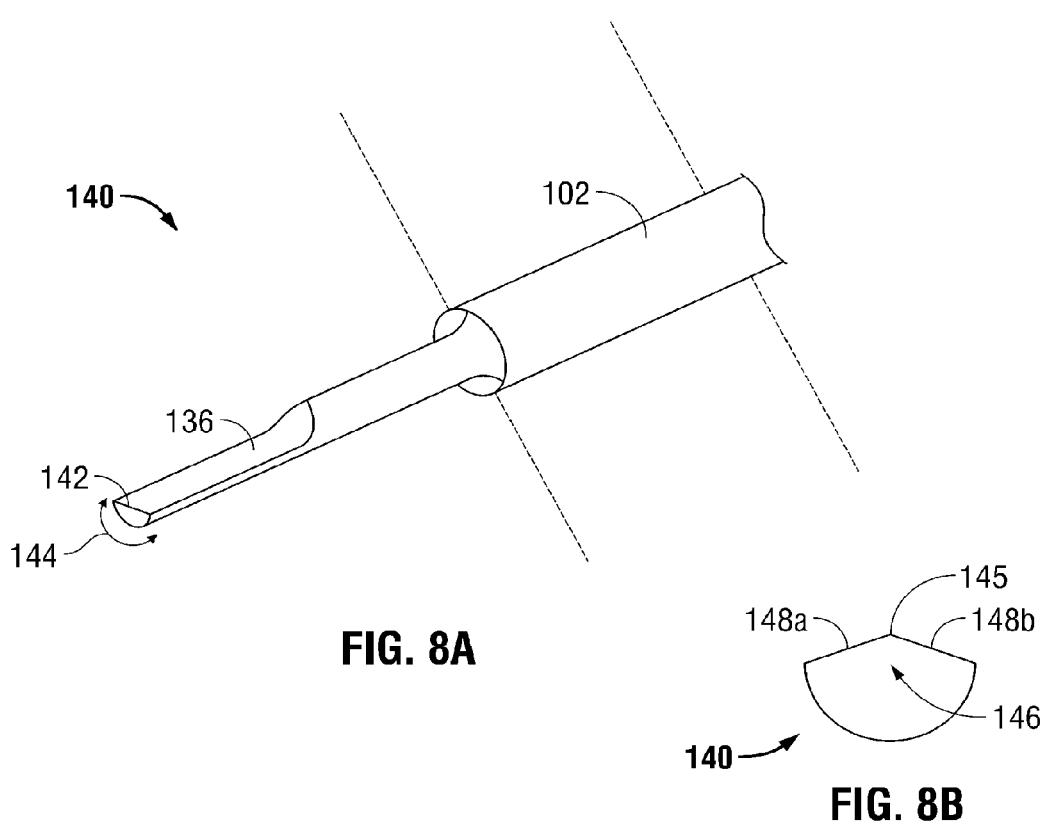
FIG. 8A
FIG. 8B

ULTRASONIC TRANSDUCER SYSTEM

PRIORITY

This application is a divisional of patent application Ser. No. 12/994,037 filed on Nov. 22, 2010 which is a US national stage patent application claiming priority under PCT Article 22(1) to a patent application entitled "Ultrasonic Transducer System" having International Application Number PCT/GB2009/001281 filed on May 21, 2009 and International Publication Number WO 2009/141618 A2 published on Nov. 26, 2009. The PCT applications claims priority to an application entitled "Improved Torsional Mode Tissue Detector" filed in the UK Intellectual Property Office on May 21, 2008 and assigned patent application Ser. No. 08/092,419. The contents of the parent application, the PCT application and the UK application are hereby incorporated herein by reference in their entirety.

RELATED APPLICATION

This application is related to U.S. national stage patent application Ser. No. 12/994,029 filed on Nov. 22, 2010 entitled "Ultrasonic Transducer Dissector" claiming priority to PCT Application Number PCT/GB2009/001278 and the UK Application Number 0809243.9. The contents of these applications are hereby incorporated by reference herein in their entirety.

BACKGROUND

1. Field of the Related Art

This disclosure relates to a surgical tool, and, more particularly, to a system and method for cutting tissue by utilizing ultrasonically vibrating blades of the surgical tool.

2. Description of the Related Art

In the past few decades, considerable interest has been directed toward the use of ultrasonically activated blades and shears for the dissection, cutting, and welding of soft tissue.

It is known to cut tissue by means of ultrasonically vibrated knives or scalpels. When a scalpel cuts tissue its effectiveness is indicated by the cutting force. This derives from the pressure required to separate the structure and from the frictional drag as the blade is drawn between the cut sections. Vibrating the blade can reduce friction and may also reduce the bond strength of the tissue. Both objectives could be achieved by applying vibrations to the cutting blade in either a longitudinal or a torsional mode.

Haemostatic cutting of individual vessels and well vasculated tissue has been taught by U.S. Pat. Nos. 3,636,943 and 3,862,630. In the '943 and '630 patents, the use of ultrasonic energy in the form of mechanical vibrations is transmitted by a tool member to close off small severed blood vessels, such as in humans, by the formation of closures at the terminal portions thereof, and stop what is referred to as "ooze," that requires constant mopping or cleansing techniques during an operation. Such tool member may be in the form of a knife ultrasonically vibrated to simultaneously sever and close off respective terminal portions of the severed blood vessels while performing surgical procedures. The tool member, of a proper configuration, may also join together layers of tissue, including the walls of unsevered blood vessels, and with respect to the latter is foreseen as replacing the "tying off" of arteries and veins currently necessary in surgery. Thus, these patents use a longitudinal mode system to activate a blade, which has roughened surfaces in order to increase frictional energy transfer during the cutting of vascular tissue.

Additionally, U.S. Pat. Nos. 5,322,055 and 6,283,981 disclose oscillatory systems with the addition of hinged passive elements designed to press the target tissue against an energized blade so as to increase the frictional drag of tissue on the blade, and, thus, increase the heating effect necessary to ensure coagulation during the cutting process.

The '055 patent relates to an ultrasonic surgical apparatus that includes a surgical instrument having a hand piece with a transducer for converting an electrical signal into longitudinal vibratory motion of a blade connected to the hand piece and an accessory releasably connected to the hand piece to enable clamping of tissue against the vibrating blade to afford improved coagulating and cutting of tissue. Scissors-like grips actuate a pivoted clamp jaw along one side of the ultrasonically vibrating blade to compress and bias tissue against the blade in a direction normal to the direction of longitudinal vibratory movement. The clamp jaw and blade are rotatable relative to one another to align a selected blade edge of a multi-edged blade with the clamp jaw for cutting and coagulating while clamping or circumferentially spacing a selected blade edge from the clamp jaw for cutting and coagulating without clamping.

The '981 patent relates to a method of designing a balanced ultrasonic surgical instrument including an ultrasonic transmission rod and an asymmetric ultrasonically actuated blade attached to the distal end of the ultrasonic transmission rod. The ultrasonically actuated blade includes a treatment portion. The treatment portion has a functional feature such as, for example, a curved blade which makes the treatment portion asymmetric. In such method, a balance portion including at least a first asymmetric balance feature is designed and positioned between the ultrasonically actuated blade and the ultrasonic transmission rod to balance out any undesirable torque generated by the treatment portion.

All of the above-described systems share the common principle of frictionally generated heating, related to cyclic vector reversal at the friction interface, to ensure that coagulation occurs simultaneously with tissue separation. In such systems, the frictionally generated heating principle is described in terms of longitudinal excitation of the cutting blade. However, pure longitudinal excitation is not the most efficient manner to transfer vibrational energy into soft tissue.

Moreover, in U.S. Pat. No. 6,425,906 and GB 2,371,492, it is noted that Young and Young first disclosed the use of different vibrational modes specifically chosen to take advantage of direct compression wave transmission into target tissue with its unique capacity to generate cavitation as the main form of energy dissipation. Specifically, such patents were the first to disclose a system and method for using torsional excitation to transfer vibrational energy into soft tissue.

For example, the '906 patent relates to a surgical tool for cutting and/or coagulating tissue that includes a piezoelectric driver to generate ultrasonic energy including torsional mode vibrations. The '906 patent also relates to a distal torsional mode end effector, which creates focused energy transmission into target tissue trapped by a hinged jaw element against an activated waveguide.

In the GB 2,333,709 patent, the use of multi-wavelength torsional mode waveguides is disclosed in relation to minimally invasive general surgical procedures. In the '709 patent, mechanisms of energy transfer are described that relate specifically to shear mode torsional systems and the conventional compression wave longitudinal equivalents.

The '709 patent further discloses that excitation of a waveguide having a length greater than 7 or 8 times the half wavelength for shear mode transmission creates issues, which are exaggerated relative to those experienced in similar compression wave systems.

Thus, while it is known to use torsional excitation to transfer vibrational energy into soft tissue, it is still desirable to produce further surgical tools that effectively manipulate torsional mode excitation.

SUMMARY

In an embodiment of the present disclosure, a transducer is presented including a horn having a first diameter; a threaded element having a second diameter; a transducer stack having a third diameter and including a plurality of rings; and a back plate positioned adjacent to the transducer stack; wherein the threaded element is positioned between the horn and the transducer stack to selectively enable torsional tuning adjustments of the transducer.

In another embodiment of the present disclosure, a method for tuning a transducer is presented including positioning a threaded element between a horn and a transducer stack; and selectively enabling torsional tuning adjustments of the transducer based on the positioning of the threaded element; wherein the horn has a first diameter, the threaded element has a second diameter, the transducer stack has a third diameter, includes a plurality of rings, and is positioned adjacent to a back plate.

In another embodiment of the present disclosure, a method for manufacturing a transducer is presented including positioning a threaded element between a horn and a transducer stack; and selectively enabling torsional tuning adjustments of the transducer based on the positioning of the threaded element; wherein the horn has a first diameter, the threaded element has a second diameter, the transducer stack has a third diameter, includes a plurality of rings, and is positioned adjacent to a back plate.

The present disclosure also provides a computer-readable medium which stores programmable instructions configured for being executed by at least one processor for performing the methods described herein according to the present disclosure. The computer-readable medium can include flash memory, CD-ROM, a hard drive, etc.

BRIEF DESCRIPTION OF THE DRAWINGS

Various embodiments of the present disclosure will be described herein below with reference to the figures wherein:

FIG. 7 is an isometric schematic diagram of a curved end effector in a torsional mode waveguide configuration shown in FIG. 6, in accordance with the present disclosure;

FIG. 8A is an isometric schematic diagram of a welder end effector in a torsional mode waveguide configuration, in accordance with the present disclosure;

FIG. 8B is a detailed front view of the distal end of the end effector, in accordance with another exemplary embodiment of the present disclosure;

DETAILED DESCRIPTION OF THE PREFERRED EMBODIMENTS

Figure 1A:
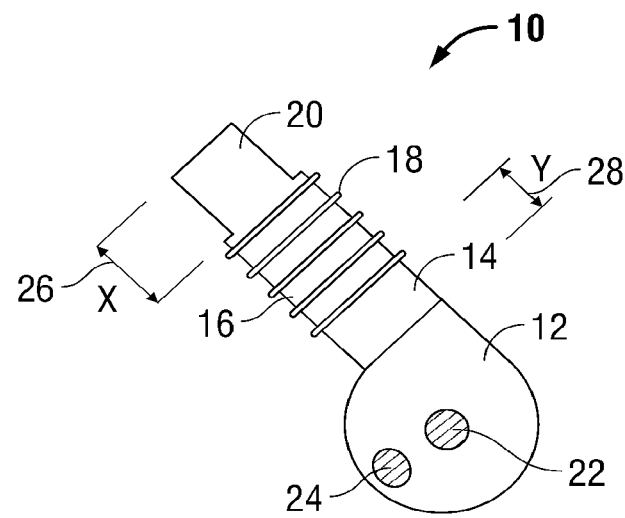
FIG. 1A is a schematic diagram of a torsional mode transducer having an extended stack to facilitate frequency matching to a horn, in accordance with the present disclosure.

Referring now to the drawing figures, in which like references numerals identify identical or corresponding elements, a system and method for cutting tissue by using torsional mode excitation in accordance with the present disclosure will now be described in detail.

While embodiments of the present disclosure are susceptible to various modifications and alternative constructions, certain illustrated embodiments thereof have been shown in the drawings and will be described below in detail. It should be understood, however, that there is no intention to limit the embodiments of the present disclosure to the specific form disclosed, but, on the contrary, the embodiments are intended to cover all modifications, alternative constructions, and equivalents falling within the spirit and scope of the present disclosure as defined in the claims.

The present disclosure may be understood more readily by reference to the following detailed description of the disclosure taken in connection with the accompanying drawing figures, which form a part of this disclosure. It is to be understood that the disclosure herein is not limited to the specific devices, methods, conditions or parameters described and/or shown herein, and that the terminology used herein is for the purpose of describing particular embodiments by way of example only and is not intended to be limiting of the claimed subject matter.

The present disclosure proposes utilizing torsional ultrasound for efficiently transferring vibrational energy into soft tissue. Unlike any other ultrasonic tools, the surgical tool of the exemplary embodiments directs powerful compression energy into the target tissue, resulting in secure coagulation and fast cutting. Away from these compression grooves, only relatively less efficient frictional energy is present. This is minimized further through a fine polishing process that reduces the risk of transferring unwanted energy into vital structures and significantly reduces the likelihood of fatigue failure with low gain. The surgical tools of the exemplary embodiments direct compression energy into the target tissue. Energy is transferred quickly, denaturing the tissue protein and rapidly forming a coagulum. At the same time the central blade cuts through the tissue as the jaw of the surgical tool is closed. The result is fast and efficient haemostatic cutting.

The present disclosure further proposes emphasizing the fundamental advantages of torsional mode systems over conventional longitudinal extensional devices. The present disclosure further addresses the characteristics of torsional dissector systems that introduce particular opening issues.

For instance, torsional mode transmission has several advantages over longitudinal mode transmission. These include, but are not limited to the following: the motional gain associated with cross sectional changes is greater in shear wave transmission than in equivalent compression wave transmission. Analysis of torsional mode concentrators reveals a gain dependence on moments of inertia associated with section changes along the transforming element. In contrast, compression wave transmission is related to linear force variation which changes with sectional area. This consideration leads to the motional gain expression for a longitudinal mode stepped transformer, defined as the square of the diameter ratio between input and output sections, and for the shear wave equivalent, the third power of the diameter ratio. This characteristic is consistent with increased Q and impedance transformation ratio for shear wave systems relative to compression wave equivalents. Thus, tuning to resonance requires more critically refined generator circuitry and tuning algorithms capable of differentiating between sharply defined resonance features.

Another distinguishing feature between longitudinal and torsional mode systems relates to transducer design. Transducer designs are specific to particular modes. The classic Langevin sandwich transducer is conventionally used to generate and sustain compression waves in a longitudinal mode system. In contrast, a mode converting horn with tangentially attached transducer stack is configured to generate a torsional output from the narrow end of the horn. The transducer stack is driven in a selected flexural mode to generate a torsional mode in the horn. Alternative flexural stack modes result in a substantially longitudinal output from the mode converter. As a result, in each case pure torsional or longitudinal modes depend on the design of the waveguide attached at the output of the horn. Operating frequencies generally result in overtone modes with waveguides spanning several wavelengths. The relationship between the horn and transducer stack renders the oscillatory system susceptible to complex transverse modes occurring in the horn and waveguide assembly. Careful and accurate control of the drive frequency is required to excite the correct mode and lock the correct mode by the generator frequency/mode control circuitry. The exemplary embodiments described below illustrate how to control a drive frequency to fine-tune resonance features and excite a desired mode for a surgical tool.

Embodiments will be described below while referencing the accompanying figures. The accompanying figures are merely examples and are not intended to limit the scope of the present disclosure.

Referring to FIG. 1A, a schematic diagram of a torsional mode transducer having an extended stack to facilitate frequency matching to a horn, in accordance with the present disclosure is presented.

The torsional mode transducer 10 of FIG. 1A includes a horn 12, a threaded element or spacer element 14, ceramic rings 16, electrodes 18, a back plate 20, a first sensor 22, and a second sensor 24. The length, X, of the back plate 20 is designated as 26 and the length, Y, of the threaded element 14 is designated as 28.

Figure 1B:
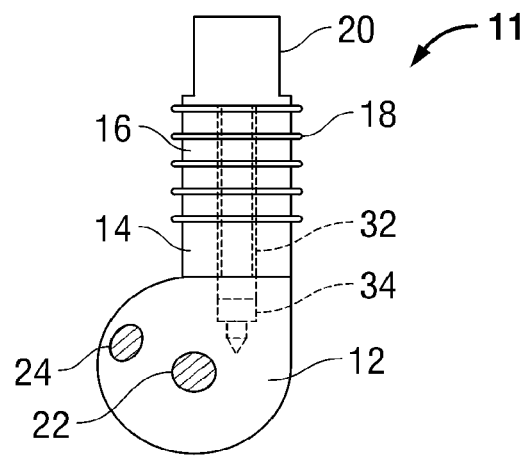
FIG. 1B is a schematic diagram of a torsional mode transducer having an extended stack with a threaded spigot located in a tapered hole, in accordance with the present disclosure.

In an exemplary embodiment of the present disclosure, the transducer 10 permits the generation of either longitudinal vibrations or pure torsional waves. Transducer 10 includes a transducer stack, comprising a number of axially polarized PZT ceramic rings 16, separated by silver or gold plated brass electrodes 18 and is compressively attached to a tangential face of the transducer 10 via spigoted back plate 20, with threaded spigot 32 located in tapped hole 34 (as shown in FIG. 1B).

Moreover, FIG. 1A shows at least two piezo-electric sensors, a first sensor 22 and a second sensor 24 located on the horn 12. The sensors 22 and 24 are located so that they respond selectively to torsional and longitudinal horn modes. In the former, the waveform from each piezo-electric sensor 22, 24 will be phase shifted according to the change in torsional displacement from the sensors of the horn where it is at a minimum, to the periphery where it is at a maximum. In the presence of a longitudinal mode, both sensors 22, 24 would experience the same extensional displacement of the horn proximal end face, producing in phase outputs from the piezo-electric sensors 22, 24. The specific operation of sensors 22, 24 will be further described below with reference to FIG. 11.

Furthermore, threaded element 14 may be designed to be any length 28. The length 28 of the threaded element 14 may be varied based on a plurality of factors, such as, but not limited to, the material of the horn 12 and the natural resonant frequencies of one or more components of the transducer 10 (e.g., horn 12, stack assembly, and/or waveguide 56). The threaded element 14 may be varied between a few millimeters up to 20 mm depending on the desired application. The length 28 of the threaded element 14 affects the output of the horn 12. In other words, by varying the length 28 of the threaded element 14 one skilled in the art may produce a desired vibration or wave (e.g., a torsional wave, a pure torsional wave, a longitudinal wave, a flexural mode wave or a combination of these waves). Additionally, the length 26 of the back plate 20 may be varied between a few millimeters up to 20 mm depending on the desired application and may also affect the type of wave produced by the horn 12. Preferably, the smaller the length 28 of the threaded element 14, the better the achievement of the desired excitation or mode. For example, the length 28 of the threaded element 14 may be in the range of 2-10 mm.

Once again, the insertion of the threaded element 14 enables an optimization of the realization of pure torsional mode as the output of the horn 12 and enables an accurate method of fine-tuning a surgical tool/device to a user's desired specifications. Also, threaded element 14 may be adjusted prior to assembly or after (subsequently) assembly of the transducer 10 to an external device (e.g., such as a waveguide 56 described below with reference to FIGS. 4 and 5). Also, threaded element 14 may have a variety of different uniform or non-uniform shapes. The substantially cylindrical shape in the Figures is merely illustrative.

Thus, in accordance to FIG. 1A, a drive frequency may be controlled to fine-tune resonance features and excite a desired mode for a surgical tool by adding a threaded element 14 between the horn 12 and the transducer stack of the transducer 10. Additionally, FIG. 1A defines means for varying the stack assembly properties, which in turn define the modal characteristics of the horn 12. The ability to optimize the torsional output from the transducer 10 is enhanced by providing or enabling this tuning facility at each end of the stack assembly.

Referring to FIG. 1B, a schematic diagram of a torsional mode transducer having an extended stack with a threaded spigot located in a tapered hole, in accordance with the present disclosure is presented.

Torsional mode transducer 11 is substantially similar to torsional mode transducer 10 and thus will only be discussed further herein to the extent necessary to identify differences in construction and/or use. The torsional mode transducer 11 of FIG. 1B includes a horn 12, a threaded element 14, ceramic rings 16, electrodes 18, a back plate 20, a first sensor 22, and a second sensor 24. Additionally, the transducer 11 includes a threaded spigot 32 located in a tapered hole 34.

As shown in FIG. 1A, the transducer stack/assembly includes a threaded element 14 inserted between the transducer stack and the horn 12. As shown in FIG. 1B, to facilitate attachment of the threaded element 14 to the horn 12, spigot 32 is extended to accommodate attachment of threaded element 14. This feature allows the resonant characteristics of the complete stack incorporating threaded element 14 to be tuned by adjusting the overall length of the transducer stack prior to attachment to the horn 12. Threaded element 14 may be either parallel-sided or tapered in section towards its distal end. Preferably horn 12 is a tapered horn.

Figure 1C:
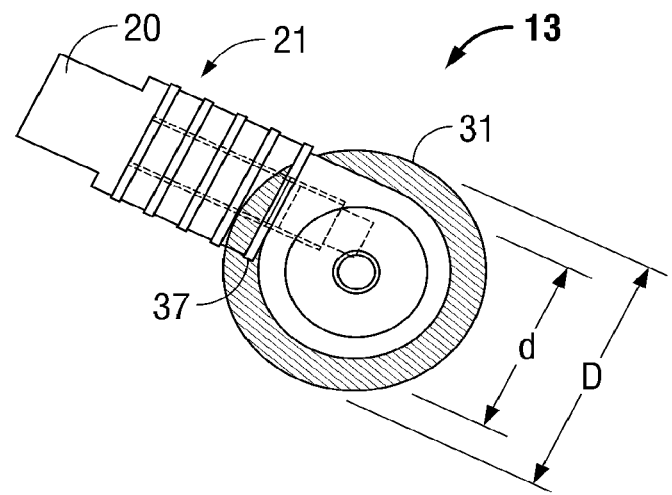
FIG. 1C is a schematic diagram of a torsional mode transducer illustrating critical dimensions of the transducer with a circumscribed cylinder from which a major component is machined.

Referring to FIG. 1C, a schematic diagram of a torsional mode transducer illustrating critical dimensions of the transducer with a circumscribed cylinder from which a major component is machined is presented.

Figure 2:
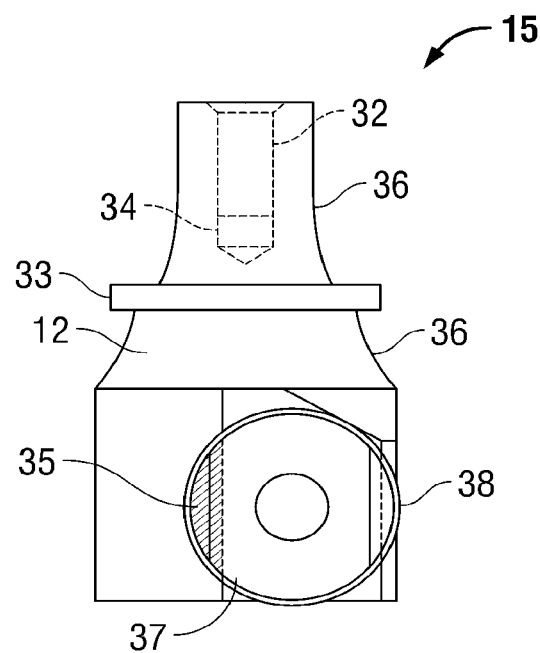
FIG. 2 is a schematic diagram of an axial view of a torsional mode transducer.

The torsional mode transducer 13 includes a stack assembly 21 disposed between the back plate 20 and a cylindrical surface 31. The stack assembly 21 abuts the cylindrical surface 31 via abutment member 37 mounted on one tangential face created by machining the shaded region of the circumscribing cylindrical surface 31 of FIG. 1C. FIG. 1C and FIG. 2 (described below) illustrate dimensional definitions transducers 13, 15. FIG. 1C defines circumscribing surface 31 which sets a tangential mounting plane of the stack assembly 21. A flexural rotation of the stack assembly 21 through angle, θ, (designated as element 44 in FIG. 3), generates a torque about the horn axis O, thus driving the horn 12 into a torsional mode.

Referring to FIG. 2, a schematic diagram of an axial view of a torsional mode transducer is presented.

The torsional mode transducer 15 includes a threaded hole 34 for waveguide attachment. Additionally, the transducer 15 includes exponential tapering surfaces 36, cylindrical extremity 38, cylindrical isolating flange 33 located adjacent to the horn 12, shaded area 35, and the abutment member 37.

Horn 12 is machined with exponential tapering surfaces 36 and interrupted by cylindrical isolating flange 33, where the exponential tapering surfaces 36 are cut tangentially to circumscribing cylindrical surface 31 (see FIG. 1C). Moreover, stack assembly 21 (see FIG. 1C) is disposed adjacent to horn 12 so that's its cylindrical extremity 38 coincides with an outer extremity of a tangential face of the horn 12 and overlaps an inner extremity as indicated by the shaded area 35.

Figure 3:
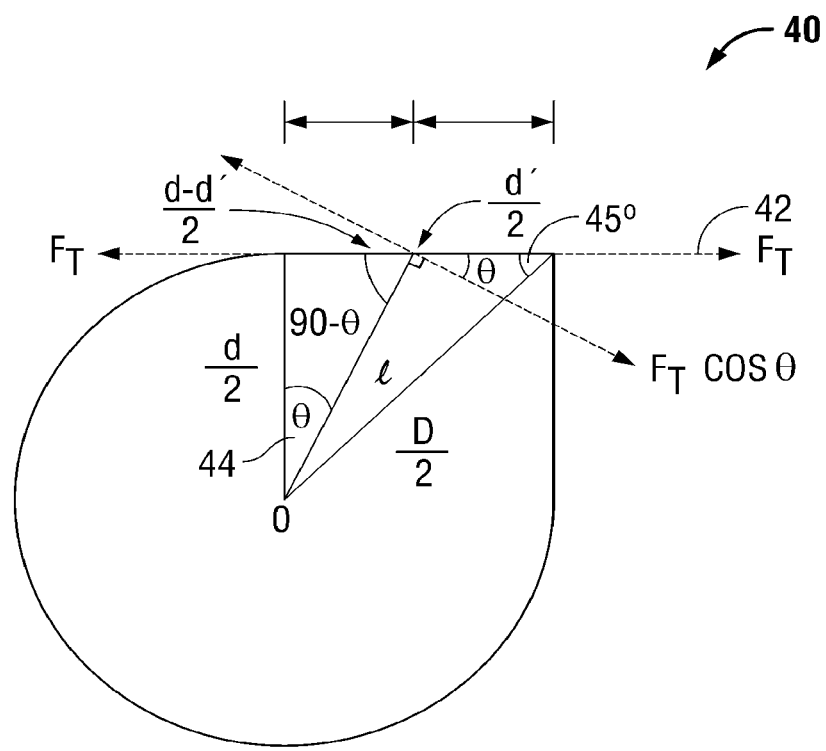
FIG. 3 is a schematic diagram of a geometric relationship between flexural stack displacement and torsional horn displacement, in accordance with the present disclosure.

Referring to FIG. 3, a schematic diagram of a geometric relationship between flexural stack displacement and torsional horn displacement, in accordance with the present disclosure is presented.

The geometric relationship 40 of FIG. 3 illustrates stack displacement 42 and an angle, θ, designated as 44.

Transducer 10 having the stack assembly is located on horn 12 so that its cylindrical extremity coincides with the outer extremity of a tangential face of the horn 12. The relationship between the stack diameter, d', the proximal horn effective diameter d, and the circumscribed diameter D are chosen critically in order to generate the required vibrational mode and resonant frequency.

Rotational movement of the proximal horn mass is initiated by a flexural mode displacement within the stack assembly as illustrated in FIG. 3. This mode is possible when d'>d/2, allowing for a more compact transducer design than employing a conventional axial mode stack where d'<<d/2. FIG. 3 illustrates the geometry which controls the transfer of stack displacement 42 to the horn 12. The equation defining the resolved component of flexural displacement $F_T$, at angle θ, 44, to mounting plane, is given as: $T = F_T \cos θ$. $l = \frac{1}{2} F_T \cos(\arctan((d-d')/d)) \cdot (d^2 + (d-d')^2)^{1/2}$.

Critical selection of d'/D ratio for optimum compact transducer operation is defined as 0.45<d'/D<0.55; preferably, 0.482; and for normal (axial mode stack) operation, 0.3<d'/D<0.4; preferably 0.333. Torsional resonance is established in either case by critical selection of a length of the horn 12, a diameter of connecting member 52 (shown in FIGS. 4 and 5) and the dimensions of the waveguide 56 (shown in FIGS. 4 and 5).

Figure 4A:
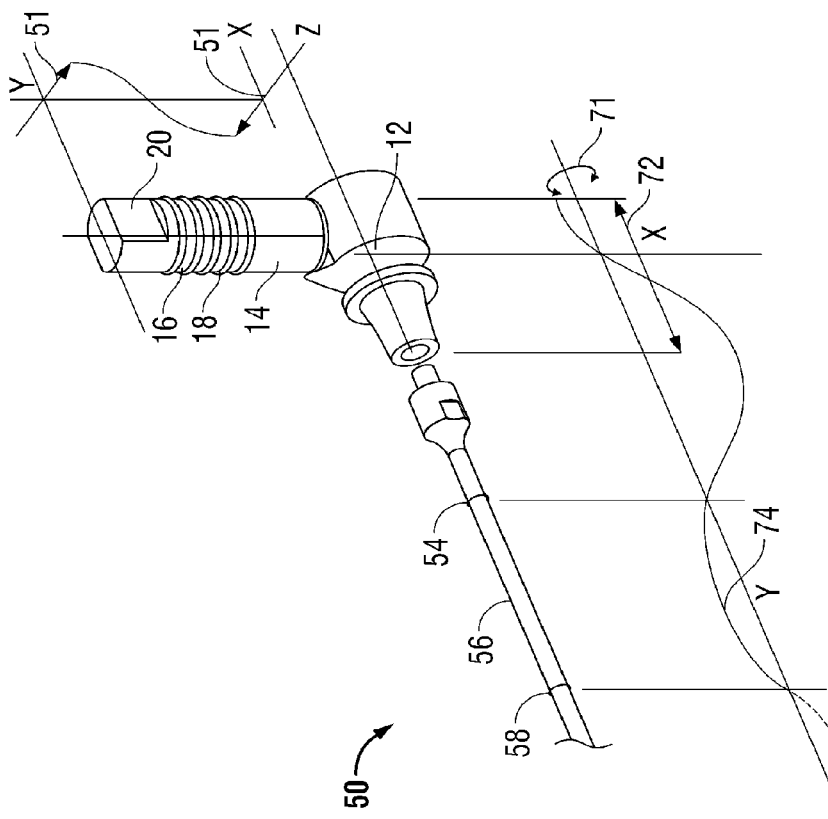
FIG. 4A is a schematic diagram illustrating a detail of the end effector of the torsional mode transducer of FIG. 4, in accordance with the present disclosure.
Figure 4A:
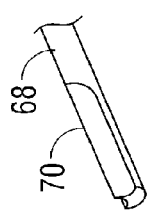
Figure 4:
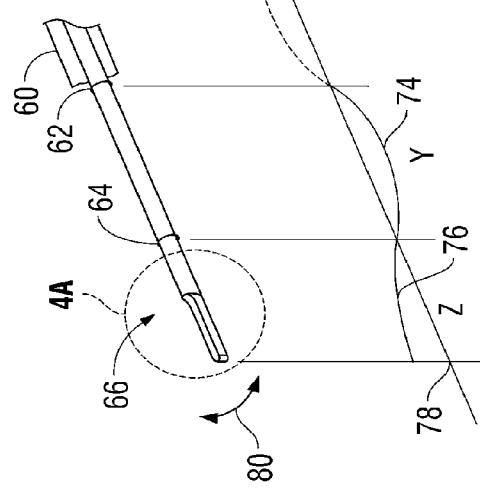
FIG. 4 is a schematic diagram of a torsional mode transducer connected to a waveguide with an illustration of the displacement amplitude distribution, in accordance with the present disclosure.

Referring to FIG. 4, a schematic diagram of a torsional mode transducer connected to a waveguide with an illustration of the displacement amplitude distribution, in accordance with the present disclosure is presented.

The transducer/waveguide configuration 50 includes torsional mode transducer 10 described above with reference to FIG. 1A. The transducer/waveguide configuration 50 further includes connecting member 52, a first nodal plane 54, waveguide 56, a second nodal plane 58, shroud tube 60, a third nodal plane 62, a fourth nodal plane 64, and an end effector 66. The end effector 66 depicts a portion of the waveguide 68 and a distal tip 70. Arrow 80 illustrates the torsional movement of the waveguide 56.

FIG. 4 further depicts a graph 71 illustrating a transmission wave that is generated when the transducer/waveguide configuration 50 is activated. A half wavelength 72 is generated between the horn 12 and the connecting member 52. A half wavelength 74 is generated between the first nodal plane 54 and the second nodal plane 58. A half wavelength 74 is also generated between the last two distal nodes 64 and 62. A quarter of a wavelength 76 is generated between the fourth nodal plane 64 and the distal tip 70 of the end effector 66. Note that the mid-section of the waveguide is omitted to save repetition, but may be typically 7 or 8 wavelengths long. FIG. 4 further depicts a graph 51 illustrating the effect of stack flexing (as described below).

Additionally, the waveguide 56 consists of an integral number of half wavelengths for shear wave propagation at the resonant frequency. Waveguide isolation is achieved by local increase in diameter coincident with nodal planes 54, 58, 62, 64, which create space between the plastic lined shroud tube 60 and active regions of the waveguide 56.

Moreover, the waveguide may be referred to as an elongated shaft having a proximal end and a distal end. In addition, the distal end may be separated into one or more sections. For example, with respect to FIGS. 6-8B, the distal end may be separated into three sections. The first section may have a first width and a first length, the second section may have a second width and a second length, and the third section may have a third width and a third length, where the first, second, and third widths are the same or different from each other. The first section may refer to an end effector, the second section may refer to a connecting section, and the third section may refer to a tip portion/blade portion of the distal end of the elongated shaft. The end effector may be a curved blade having twin grooves as illustrated in FIG. 4, element 70.

Referring to FIG. 4A, a schematic diagram illustrating a detail of the end effector of the torsional mode transducer of FIG. 4, in accordance with the present disclosure is presented. The detailed view illustrates the shape of the distal tip 70, which depicts a twin groove configuration. Of course, one skilled in the art could contemplate a plurality of different distal tip configurations to achieve either longitudinal and/or torsional excitation.

Figure 5:
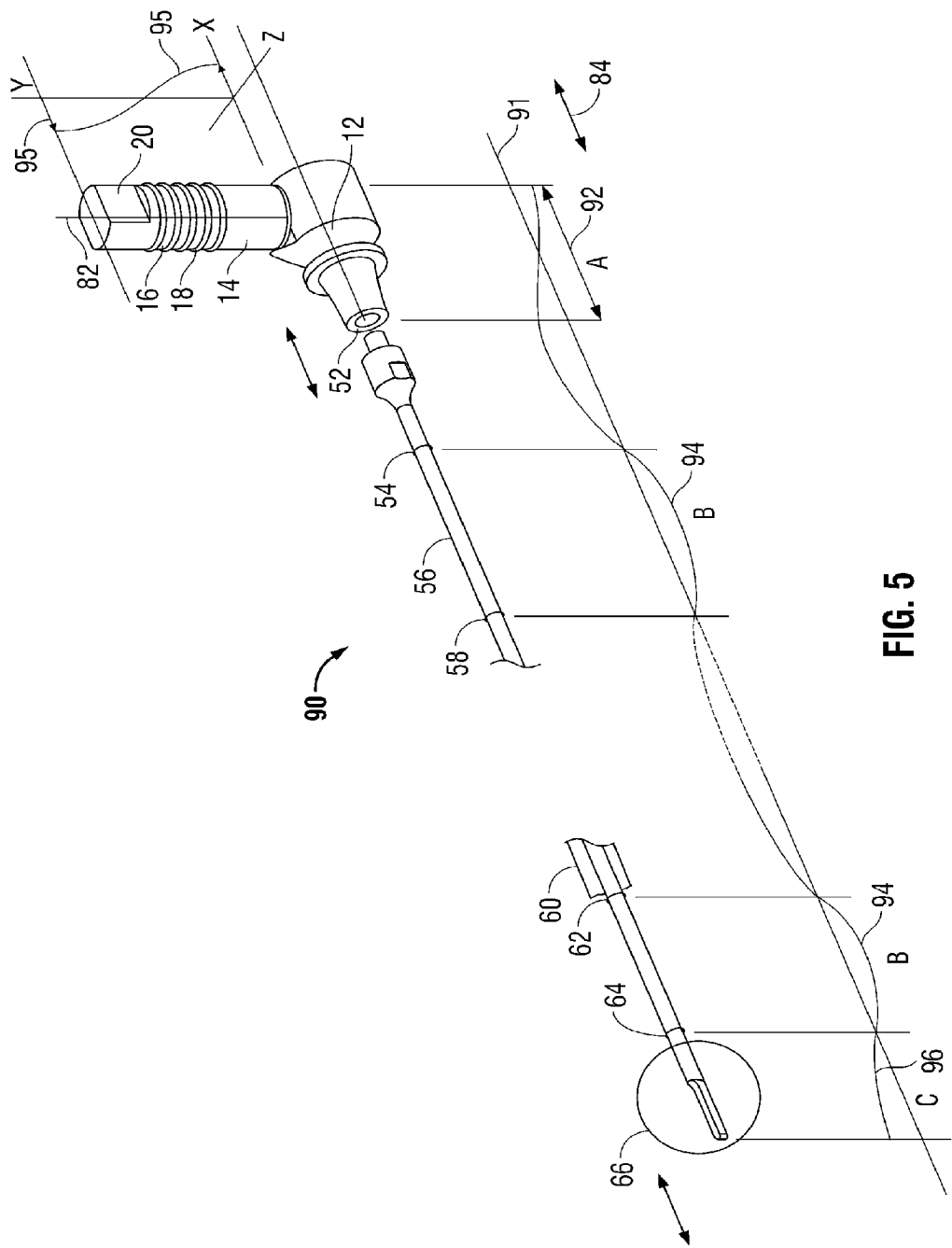
FIG. 5 is a schematic diagram of a longitudinal mode transducer connected to a waveguide with an illustration of the displacement amplitude distribution, in accordance with the present disclosure.

Referring to FIG. 5, a schematic diagram of a longitudinal mode transducer connected to a waveguide with an illustration of the displacement amplitude distribution, in accordance with the present disclosure is presented.

Transducer 90 is substantially similar to torsional mode transducer 50 and thus will only be discussed further herein to the extent necessary to identify differences in construction and/or use. Transducer 90 has a similar transmission wave graph to the transmission wave graph illustrated in FIG. 4. Graph 91 illustrates a transmission wave that is generated when the transducer/waveguide configuration 90 is activated. A half wavelength 92 is generated within the horn 12. A half wavelength 94 is generated between the first nodal plane 54 and the second nodal plane 58. A half wavelength 94 is also generated between the third nodal plane 62 and the fourth nodal plane 64. A quarter of a wavelength 96 is generated between the fourth nodal plane 64 and the distal tip 70 of the end effector 66. FIG. 5 further depicts a graph 95 illustrating the effect of stack flexing (as described below).

In the alternative exemplary embodiment, as illustrated in FIG. 5, the transducer stack assembly is activated in a variant flexural mode such that end face 82 of the back plate 20 is deflected as indicated by arrow 84 in a longitudinal direction. This stack movement generates a longitudinal mode in the horn 12 at a frequency consistent with compression wave transmission in the horn 12 and attached waveguide 56. The frequency for longitudinal resonance is related to the designed torsional mode frequency by the expression: $F_{tor}/F_{long}=G/E$, where, G, is the shear modulus and, E, is Young's modulus for the horn 12 and waveguide material.

These features (i.e., threaded element 14 incorporated in the transducer 10 and nodal planes 54, 58, 62, 64) allow a surgical tool system to be driven alternately in either longitudinal or torsional modes with the possibility of generating an increased distal length of effective displacement, with the advantage that there is no need for an additional transducer stack attached to the horn proximal end face to create the longitudinal displacement as taught in Young and Young, the dual mode application, issued as GB Patent No. 2,438,679. Moreover, nodal bosses or nodal planes 54, 58, 62, 64 machined on the waveguide 56 provide a simple means of acoustic isolation of the waveguide 56 from the mounting tube(s) 160, which allow the torsional/longitudinal resonance to be deployed with a cooperative hinged jaw 182 (see FIG. 9).

In both FIGS. 4 and 5, the transducer configurations 50, 90 can generate either longitudinal or torsional resonance in a tuned multi half wave rod system attached to the narrow end of the horn 12. FIGS. 4 and 5 illustrate the relative effects of two flexural stack modes in orthogonal planes, as shown in graphs 51, 71, 91, 95. Specifically, graphs 51 and 95 illustrate the effect of the stack flexing in the YZ plane which generates a torsional mode in the horn 12 and the waveguide 56. When excited at a different frequency, exciting flexure in the XY plane of FIG. 5, the output is longitudinal. FIGS. 4 and 5 further illustrate the potential to generate two different modes alternately at different frequencies, which are selected to produce torsional and longitudinal wavelengths with a number of coincident nodal planes 54, 58, 62, 64. The ability to tune the stack assembly allows one skilled in the art to optimize either longitudinal or torsional outputs and also to combine them with an appropriate switched, dual frequency electrical generator (as described below with reference to FIGS. 11 and 12).

Essentially, the stack assembly and the horn 12 determine the mode of vibration and the waveguide 56 is tuned to resonate in a particular mode by adjusting its length to encompass a number of half wavelengths at one or more designated frequencies. Furthermore, graph 51 shows a stack mode which generates a rotational mode in the horn 12, creating torsional resonance in the waveguide 56, indicated by arrows 71 and 80. The horn 12 always embodies a half wave length with antinodes at both ends.

Moreover, the nodal planes 54, 58, 62, 64 are established as part of the resonance displacement pattern and are used to provide mechanical isolation by incorporating local bosses on the waveguide 56. These create gaps between the waveguide 56 and the plastic shroud liner (see FIG. 9). FIGS. 4 and 5 both serve to illustrate the relationship between the stack flexural mode (plane XY longitudinal and YZ torsional) and the waveguide mode. FIG. 4 illustrates a torsional system, whereas FIG. 5 illustrates a longitudinal system. The only difference in the waveguide 56 is that the compression half wave length is greater than the torsional since compression wave velocity is greater than shear velocity for a given material.

The prior art of Young and Young, GB 2423931, teaches the use of a torsional mode dissector with a curved distal end effector substantially tapered from the distal tip and with only relatively short focusing grooves towards the proximal blade end. This lack of distal focusing grooves reduces the coagulating efficiency of the tip of the curved blade although it permits some lateral tissue welding capability.

Figure 6:
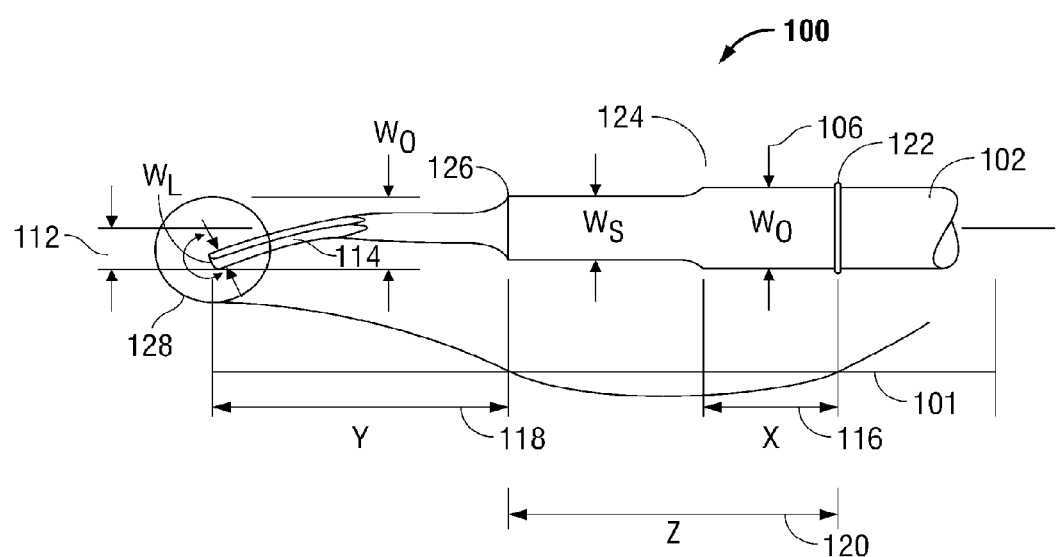
FIG. 6 is a schematic diagram of an axial view of a curved end effector in a torsional mode waveguide configuration, in accordance with the present disclosure.

It is one objective of the exemplary embodiments illustrated in FIGS. 6 and 7 to create a torsional mode curved end effector 100, 130 with a full distal focusing feature. FIGS. 6 and 7 will be simultaneously described.

FIG. 6 illustrates curved end effector 100 in accordance with the present disclosure, which comprises three distal waveguide regions; a proximal first portion 102 of section Wo, which would attach to a torsional waveguide and transducer as defined in FIG. 4; a half wavelength second distal section extending from nodal isolating boss 122, through quarter wave anti-nodal step 124 to first distal nodal step 126 of section Ws; and a third distal quarter wavelength region extending from distal step 126 to torsional blade tip 128 of section Wl. The third section embodies a double grooved focusing region 114, similar to that illustrated in FIG. 4A and defining the extent of the distal blade.

The end effector waveform is shown schematically as 101 in FIG. 6, where the second effector region of length Z, 120, is shown to be a half wavelength, with initial length X, 116, terminating in anti-nodal step 124.

The anti-nodal step has a zero amplitude gain characteristic, which in conjunction with nodal gain step 126, permits control of the critical torsional displacement amplitude within curved blade region 114.

It is another objective of the exemplary embodiments of the present disclosure, to minimize transverse modes created by the inertial effect of the axially offset mass associated with the curved effector blade, which in FIG. 6 is offset from the waveguide axis by a distance 112. Clearly, by reducing the diameter of the distal blade section 114, relative to the input section Wo, 102, the inertial moment which generates unwanted transverse modes, is reduced.

The limits satisfying this criterion are expressed by the inequality: 1.5<Wo/Wl<3.0. Inclusion of the zero gain anti-nodal step 124 allows one skilled in the art to limit the peak distal blade amplitude to 200 microns by relying on the amplitude gain at 126. The nodal torsional gain is found from the expression: Gain, $K=(Ws/Wl)^3$. The above consideration permits blade curvature and peak displacement amplitude to meet operating criteria for acceptable haemostatic tissue dissection. Blade curvature is controlled so that the distal tip is constrained to lie within the cylindrical envelope defined by section Wo at 106.

The magnitude of the waveguide section steps at 124, 126 and any non-linear variation in the section along Y, 118, in FIG. 6, can clearly be varied independently to control the output characteristics of the waveguide, thus allowing high rotational amplitudes with minimum harmful transverse modes. It is noted that the above expressions serve as an exemplary definition only and do not limit scope for wider application of the present disclosure.

FIGS. 8A and 8B are schematic illustrations of a further aspect of the present disclosure intended to optimize the use and effectiveness of the torsional mode transducer, waveguide, and end effector system referred to throughout the present disclosure, in a particular surgical process which involves tissue welding as an end point objective. In this function, the elements of the end effector structure, which focus energy into the target tissue, for example, a specific large blood vessel, are emphasized whilst at the same time changing the detail of features which encourage tissue separation in order to delay or prevent that process.

FIG. 8A shows a welder end effector 140 attached to waveguide 142 at nodal step plane 134. The section change at the nodal step creates sufficient torsional amplitude gain, according to the principles described earlier, to enable the tissue contacting face 136 to direct energy into the target vascular tissue. FIG. 8B shows profile of end effector blade 136 which is essentially flat but may be raised centrally as shown, creating angled faces 148a and 148b which meet at ridge feature 145. Surface 36 may be close to the diametral plane of the end effector, defined by waveguide axis 146 in FIG. 8B.

The displacement amplitude of the torsional mode activation in faces 148a and 148b is maximum at the periphery and small along the central ridge 145. This characteristic generates focused ultrasound transmission into contacting tissue on either side of the ridge, thus creating a strong weld. The low energy associated with ridge 145 produces only a slow tissue separation effect delaying cutting and ensuring a fully haemostatic tissue bond in the target vessel adjacent to facets 148a and 148b.

Cutting is further slowed by employing a pulse mode electrical drive to the torsional transducers. Additionally, according to the present disclosure, and especially when using an end effector having a flat operative face, or one with a very shallow longitudinal ridge, which acts to delay or de-emphasize cutting in favor of welding or coagulating the tissue(s) with which the end effector is in contact with, the end effector can be activated with pulsed ultrasonic vibrations. Therefore, this results in pulsing the ultrasonic activation of the tool or end effector driven by the transducer. The generator is described with reference to FIGS. 11 and 12 below. The operation of ultrasonically activated dissectors and welders such as described above is greatly enhanced by the provision of a hinged cooperative jaw attached to a protective shroud which also houses a jaw articulation system. This is more fully illustrated by reference to FIGS. 9 and 10 below.

Figure 9:
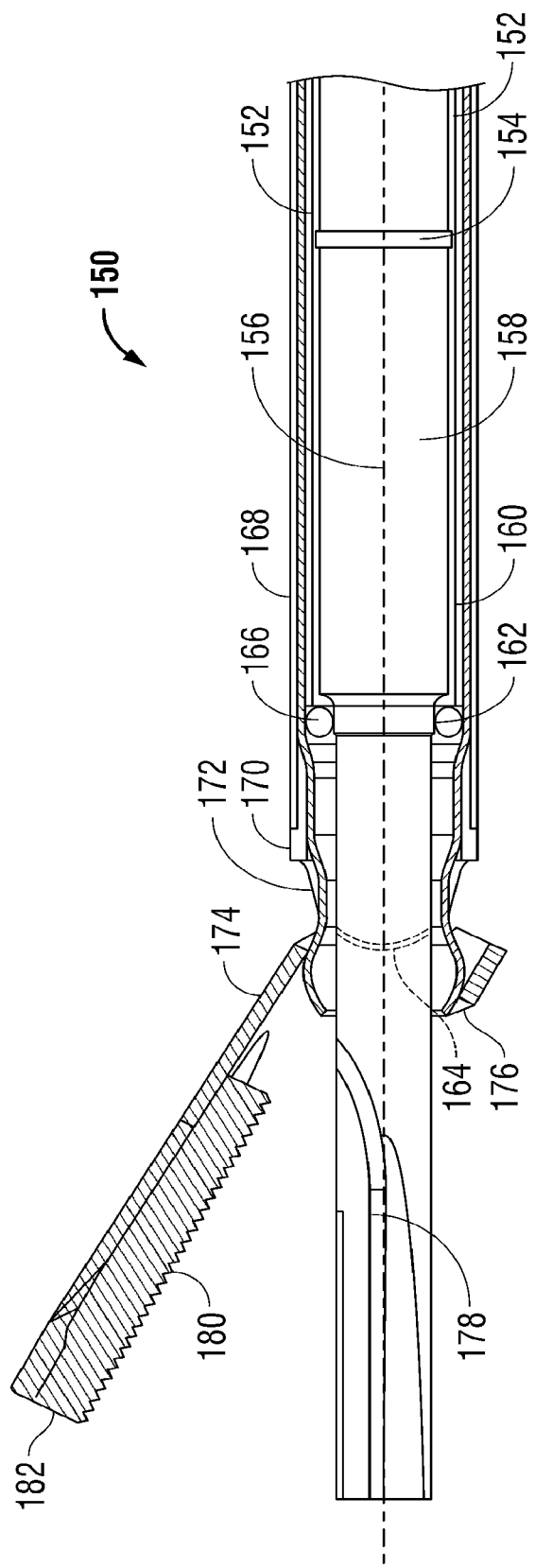
FIG. 9 is a schematic diagram of a waveguide, shroud, and hinged jaw of a torsional mode waveguide configuration, in accordance with the present disclosure.

Referring to FIG. 9, a schematic diagram of a waveguide, shroud, and hinged jaw of a torsional mode waveguide configuration, in accordance with the present disclosure is presented.

The torsional mode waveguide configuration 150 includes one or more liners 152, a separating member 154, a waveguide axis 156, a waveguide 158, a concentric tube 160, a locking member 162, an axial view of spigot(s) 164, a socket balls 166, an outer surface 168, a tube edge 170, a gap 172, a top portion 174 of jaw 182, a clamping feature 176, a first inner portion 178 of jaw 182, and a second inner portion 180 of jaw 182.

In another exemplary embodiment of the present disclosure, shown in FIGS. 9, 10A, 10B, and 10C, a torsional mode dissector head incorporating a waveguide, a co-operative jaw, a protective outer casing and an acoustic isolation system is described.

FIG. 9 depicts a distal portion of an ultrasonic tissue dissector. Jaw 182 is attached permanently to the socket balls 166 and the clamping feature 176, thus allowing the jaw 182 to rotate in a plane which is parallel to the waveguide axis 156. The present disclosure permits jaw 182 to be removably mounted to the socket balls 166, being supported on spigots 164, which engage in the locking member 162. Attachment of the jaw 182 is achieved by expanding gap 172 until the separation of the spigots 164 is sufficient to allow them to engage in the locking member 162 having socket balls 166.

Thus, a further advantage of the torsional mode waveguide configuration 150 over traditional art is the method of acoustic isolation of the waveguide 158 from the passive elements of the system, represented by concentric tube 160 and one or more liners 152.

Figure 10A:
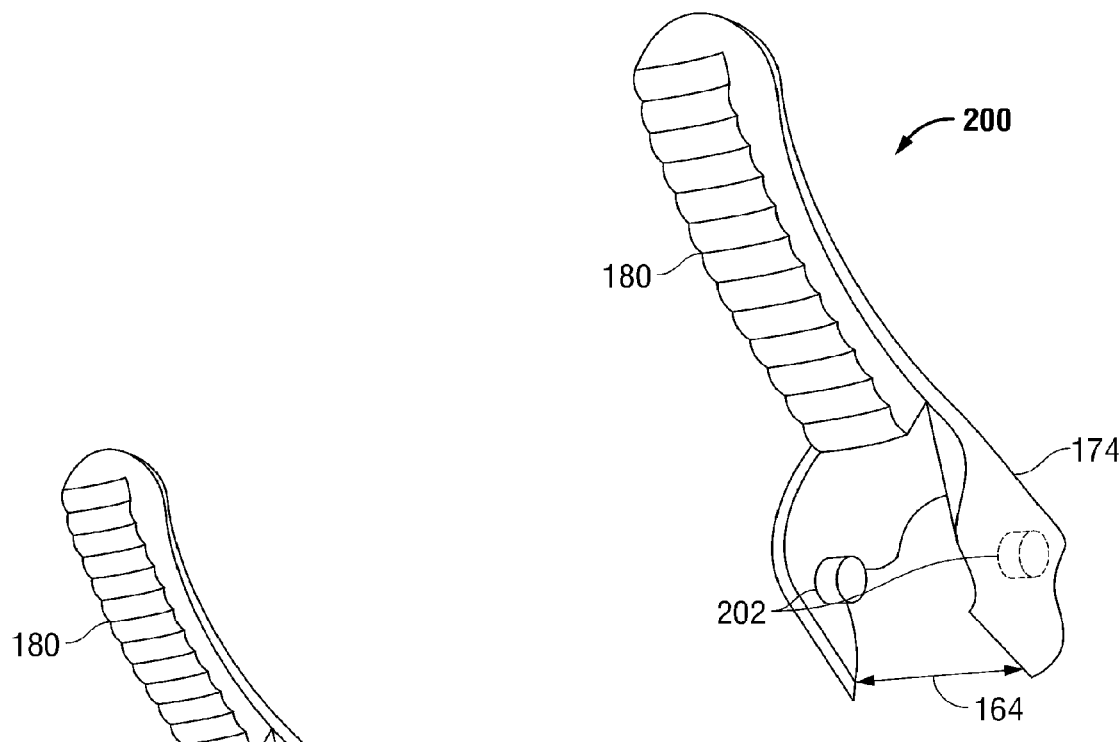
FIGS. 10A, 10B, and 10C are schematic diagrams of the jaw configuration, in accordance with the present disclosure.
Figure 10B:
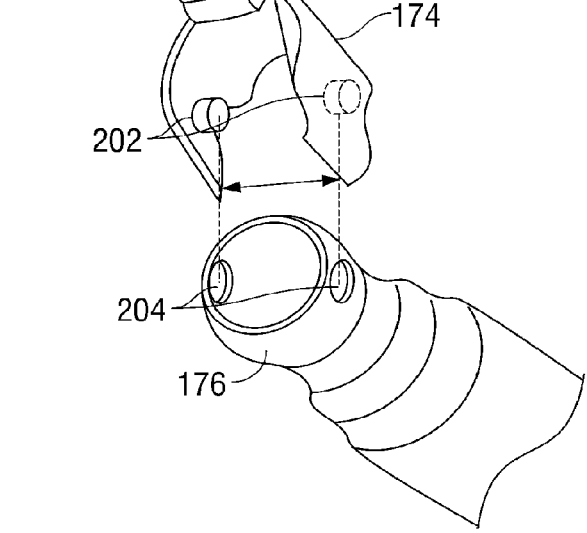
Figure 10C:
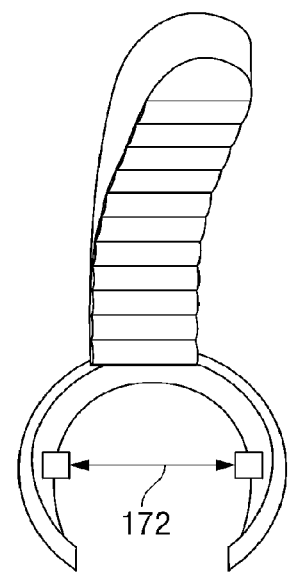

Referring to FIGS. 10A, 10B, and 10C, schematic diagrams of the jaw configuration, in accordance with the present disclosure are presented.

Jaw configuration 200 is substantially similar to the jaw portion 184 of FIG. 9 and thus will only be discussed further herein to the extent necessary to identify differences in construction and/or use. Jaw configuration 200 further includes a pair of pivot members 202 and a pair of receiving members 204.

FIG. 10A merely illustrate how the pivot members 202 fasten to the receiving members 204 of FIG. 10B. FIG. 10C merely illustrates how the gap 172 separates the ends of the jaw configuration 200 in order to provide a linking mechanism between the spigot 164, the socket balls 166 and the locking member 162.

Figure 11:
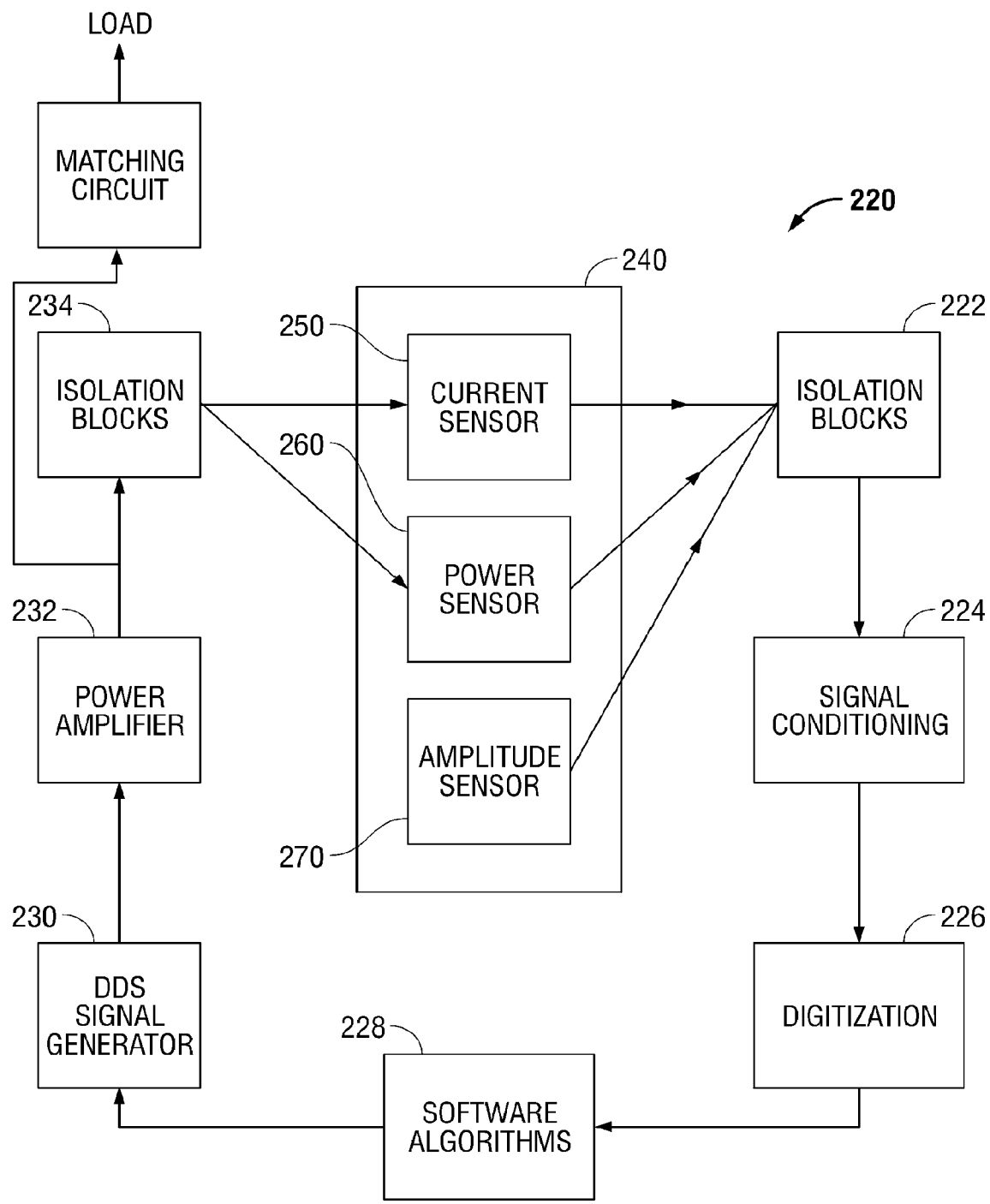
FIG. 11 is a block diagram of a first embodiment of control and power circuits for a torsional mode ultrasonic generator, in accordance with the present disclosure.

Referring to FIG. 11, a block diagram of a first embodiment of control and power circuits for a torsional mode ultrasonic generator, in accordance with the present disclosure is presented.

The block diagram 220 includes first isolation blocks module 222, signal conditioning module 224, digitization module 226, software algorithms module 228, DDS signal generator module 230, power amplifier module 232, second isolation blocks module 234, current sensor module 250, power sensor module 260, and amplitude sensor module 270. The current sensor module 250, the power sensor module 260, and the amplitude sensor module 270 may be collectively referred to as an output transducer 240.

In general, an electrical generator has the capability of driving torsional mode systems, such as the ones described in FIGS. 1-8. For example, a processor controlled DDS (direct digital synthesis) chip 230 may drive a switch mode power amplifier 232 coupled to a torsional mode transducer 240 through transformer and impedance matching inductors 250, 260, 270. The matching circuit, incorporating current and voltage monitoring components and including appropriate isolating circuitry 222, 234, is shown in FIG. 11.

To ensure correct mode selection, the output signals from the current and displacement monitoring circuits 250, 260, 270 are compared during a broad frequency scan. Transducer displacement amplitude 270 is monitored using piezo ceramic sensors 22 and 24 mounted on the horn 12, as shown in FIGS. 1 and 2. The signal from sensor 22, positioned on the horn axis, uniquely gives a minimum output when the transducer is a torsional resonance. The output from sensor 24 is a maximum at torsional resonance. By contrast the outputs from each sensor 22, 24 would be at a minimum when the horn 12 is at a longitudinal resonance.

Figure 12:
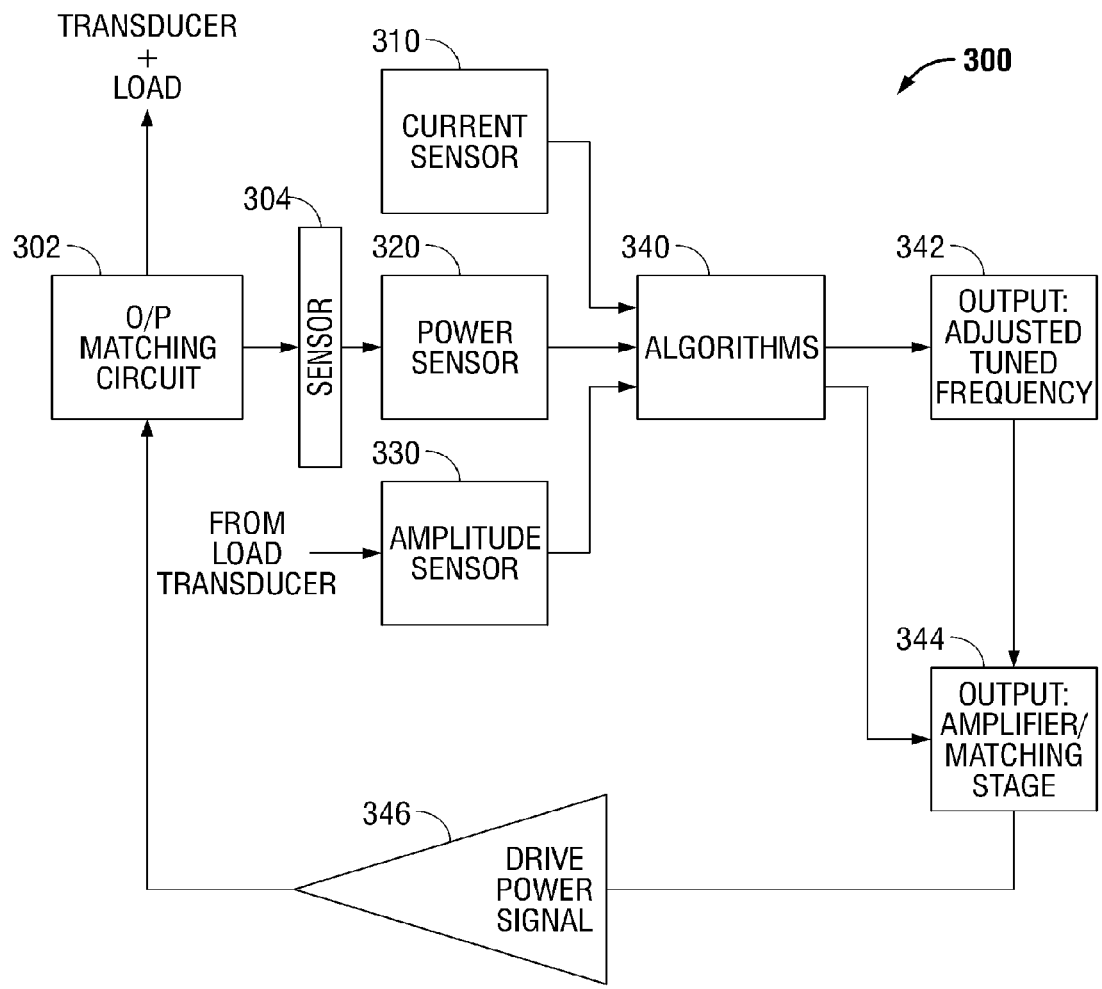
FIG. 12 is a block diagram of a second embodiment of control and power circuits for a torsional mode ultrasonic generator, in accordance with the present disclosure.

Referring to FIG. 12, a block diagram of a second embodiment of control and power circuits for a torsional mode ultrasonic generator, in accordance with the present disclosure is presented.

The block diagram 300 includes an output transducer 302, a sensor 304, a current sensor 310, a power sensor 320, an amplitude sensor 330, algorithms 340, a first output 342, a second output 344, and a drive power signal 346.

The main significance of this second embodiment of the control and power circuits for the torsional mode ultrasonic generator 300 is that it mirrors the transducer current variation as the generator frequency passes through torsional resonance. By comparing these traces it is therefore possible to detect torsional resonance with absolute certainty. Clearly, either current amplitude signals can be used as a means of effecting resonance control. However, a more useful result is obtained by using instantaneous load current and voltage to compute instantaneous power. Additionally, a tuning algorithm may then be written to select resonance coincident with maximum power and control loop algorithms may be written for coarse and fine tuning characteristics.

Figure 13:
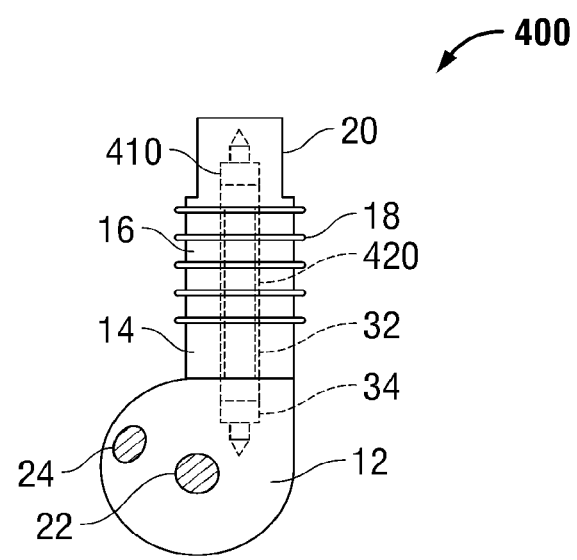
FIG. 13 is a schematic diagram of an alternative embodiment of a torsional mode transducer having an extended stack with two threaded spigots, one located at a proximal end and one located at a distal end of a threaded shaft, in accordance with the present disclosure.

Referring to FIG. 13, a schematic diagram of an alternative embodiment of a torsional mode transducer having an extended stack with two threaded spigots, one located at a proximal end and one located at a distal end of a threaded shaft, in accordance with the present disclosure is presented.

Torsional mode transducer 400 is substantially similar to torsional mode transducer 11 of FIG. 2 and thus will only be discussed further herein to the extent necessary to identify differences in construction and/or use. The torsional mode transducer 400 of FIG. 13 includes a horn 12, a threaded element 14, ceramic rings 16, electrodes 18, a back plate 20, a first sensor 22, and a second sensor 24. The transducer 400 further includes a threaded spigot 32 located in a tapered hole 34. Additionally, and in contrast to FIG. 2, the transducer 400 includes a second threaded spigot 410 on the distal end of the threaded shaft 420.

In this exemplary alternative embodiment, the threaded shaft 420 is provided with tightenable spigots 32, 410 (or nuts) at both its proximal and its distal end. This allows the stack assembly to be compressed further while still mounted to the horn 12. Also, one may use exchangeable spigots/nuts 32, 410 at the free end of the stack assembly, having different sizes and masses, the variation in mass allowing one to tune the resonant frequency produced by the stack assembly. In existing stacks, one merely builds a stack, and then checks what frequency it happens to produce and tuning can be carried out by exchanging the spigot/nut 32, but this is less convenient because one needs to separate the stack assembly from the horn 12 to access the nut 32. In contrast, having a threaded shaft 420 with opposing spigots 32, 410 allows for more versatility in assembly and manufacturing.

In conclusion, fine-tuning resonance requires more critically refined generator circuitry and tuning algorithms capable of differentiating between sharply defined resonance features. The exemplary embodiments provide for efficient fine-tuning of resonance characteristics of one or more components of a surgical tool in order to selectively provide for pure torsional vibrations/waves and/or longitudinal vibrations/waves and/or flexural vibrations/waves.

It is to be understood that the illustrated embodiments are for the purpose of example, and that numerous other configurations of transducer/waveguide assemblies exist. Accordingly, the illustrated and described embodiments are not intended to limit the scope of the inventive subject matter only to those embodiments.

It should also be understood that the transducer/waveguide arrangements described herein can be used in connection in a wide variety of applications outside the implementations described herein. For example the transducer/waveguide arrangements described herein can be used in cooperation with other known transducer/waveguide arrangements. The transducer/waveguide arrangements described herein can also be useful for non-human applications.

The present disclosure also includes as an additional embodiment a computer-readable medium which stores programmable instructions configured for being executed by at least one processor for performing the methods described herein according to the present disclosure. The computer-readable medium can include flash memory, CD-ROM, a hard drive, etc.

It will be appreciated that variations of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims. The claims can encompass embodiments in hardware, software, or a combination thereof.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

Those skilled in the art, having the benefit of the teachings of the present disclosure as herein and above set forth, may effect modifications thereto. Such modifications are to be construed as lying within the scope of the present disclosure, as defined by the appended claims.

The invention claimed is:

1. An ultrasonically-vibratable tool comprising:
   an ultrasonic horn having an elongate waveguide extending therefrom; and
   a transducer stack comprising a plurality of piezo-electric elements separated by electrodes, each piezo-electric element of the plurality being axially-polarized, said transducer stack being mounted to the horn eccentrically to a longitudinal axis of the waveguide, wherein the plurality of piezo-electric elements of the transducer stack is selectably operable to generate in the horn and in the waveguide ultrasonic vibrations having either substantially longitudinal or purely torsional vibrational modes at any instance in time.

2. An ultrasonically-vibratable tool as claimed in claim 1, wherein the tool is a surgical tool adapted for use in laparoscopic surgical methods.

3. An ultrasonically-vibratable tool as claimed in claim 1, wherein the transducer stack is operable to vibrate in a flexural mode in a plane substantially parallel to the waveguide, thereby generating longitudinal mode vibrations in the horn and the waveguide.

4. An ultrasonically-vibratable tool as claimed in claim 1, wherein the transducer stack is operable to vibrate in a flexural mode in a plane substantially orthogonal to the waveguide, thereby generating torsional mode vibrations in the horn and the waveguide.

5. An ultrasonically-vibratable tool as claimed in claim 1, wherein the transducer stack is tunable to produce in the horn and the waveguide a selected vibrational mode having a desired vibrational frequency.

6. An ultrasonically-vibratable tool as claimed in claim 1, wherein the transducer stack is tunable as to produce in the waveguide a resonant torsional mode vibration having a preselected wavelength.

7. An ultrasonically-vibratable tool as claimed in claim 6, wherein the waveguide is provided with radially outstanding spacer rings located at nodal planes of said resonant torsional mode vibration.

8. An ultrasonically-vibratable tool as claimed in claim 7, wherein the transducer stack is tunable as to produce in the waveguide a resonant longitudinal mode vibration having nodal planes coincident with those of said resonant torsional mode vibration and coincident with said spacer rings.

9. An ultrasonically-vibratable tool as claimed in claim 7, wherein said spacer rings are adapted to support a shroud surrounding the waveguide substantially isolated from vibrations therein.

10. An ultrasonically-vibratable tool as claimed in claim 1, wherein the horn is provided with at least two motion sensors, a first of said motion sensors being disposed adjacent a longitudinal axis defined by the waveguide and a second of said motion sensors being located adjacent a periphery of the horn remote from said axis.

11. An ultrasonically-vibratable tool as claimed in claim 10, wherein said motion sensors are adapted that in a torsional mode vibration of the tool a signal from the peripheral second motion sensor is phase-shifted from a signal from the axial first motion sensor, while in a longitudinal mode vibration the signal from each of said motion sensors is in phase.

12. An ultrasonically-vibratable tool as claimed in claim 11, further comprising a control circuit adapted to distinguish torsional and longitudinal mode vibrations on the basis of a difference between said signals.

13. An ultrasonically-vibratable tool as claimed in claim 12, wherein the control circuit compares a voltage, current and/or power applied to the transducer stack with a difference between the phases of the signals from the first and second motion sensors, substantially coincident maxima of each indicating a torsional mode resonance.

14. The ultrasonically-vibratable tool of claim 1, wherein the horn has generally cylindrical symmetry but comprises at least one tangential face, extending parallelly to the waveguide and tangentially to a cylindrical surface of the horn, and the transducer stack is mounted to one said tangential face of the horn.

15. The ultrasonically-vibratable tool of claim 14, wherein the transducer stack is so mounted to the horn that a cylindrical extremity of the transducer stack coincides with an outer extremity of said tangential face of the horn and overlaps beyond an inner extremity of said tangential face of the horn.

16. The ultrasonically-vibratable tool of claim 14, wherein the transducer stack has a diameter d', the horn has a proximal effective diameter d, said proximal effective diameter being taken across a proximal cylindrical portion of the horn, and d' is greater than d/2.

17. The ultrasonically-vibratable tool of claim 14, wherein the horn has a circumscribed diameter D, said circumscribed diameter being taken across a circumscribing surface encircling the horn including the tangential face, the transducer stack mounted thereto has a diameter d', and d'/D is greater than 0.45 and less than 0.55.

18. The ultrasonically-vibratable tool of claim 17, wherein d'/D equals 0.482.

19. The ultrasonically-vibratable tool of claim 14, wherein the horn has a circumscribed diameter D, said circumscribed diameter being taken across a circumscribing surface encircling the horn including the tangential face, the transducer stack mounted thereto has a diameter d', and d'/D is greater than 0.3 and less than 0.4.

20. The ultrasonically-vibratable tool of claim 19, wherein d'/D equals 0.333.

* * * * *